(12) United States Patent
Brack-Werner et al.

(10) Patent No.: US 7,183,047 B2
(45) Date of Patent: Feb. 27, 2007

(54) REPORTER GENE CONSTRUCT FOR THE DETECTION OF HIV REV AND HIV TAT

(75) Inventors: Ruth Brack-Werner, München (DE); Markus Neumann, Lohof (DE); Horst Wolff, München (DE); Volker Erfle, München (DE)

(73) Assignee: GSF-Forschungszentrum für Umwelt und Gesundheit, GmbH, Oberschleissheim (DE)

( * ) Notice: Subject to any disclaimer, the term of this patent is extended or adjusted under 35 U.S.C. 154(b) by 590 days.

(21) Appl. No.: 10/176,010

(22) Filed: Jun. 20, 2002

(65) Prior Publication Data

US 2003/0092032 A1 May 15, 2003

(30) Foreign Application Priority Data

Jun. 22, 2001 (DE) ................. 101 301 55

(51) Int. Cl.
*C12Q 1/00* (2006.01)
*C12Q 1/02* (2006.01)
*C12Q 1/68* (2006.01)
*C12N 15/33* (2006.01)

(52) U.S. Cl. .............. 435/4; 435/29; 435/320.1; 435/252.3; 435/325; 435/6; 536/23.72; 536/24.1

(58) Field of Classification Search .......... 435/320.1, 435/7.1, 6, 252.3, 325; 536/23.1
See application file for complete search history.

(56) References Cited

U.S. PATENT DOCUMENTS 5,654,398 A 8/1997 Frankel et al. ........... 530/327
6,225,045 B1 5/2001 Karn et al. ................... 435/5

FOREIGN PATENT DOCUMENTS

WO WO 99/39011 8/1999
WO WO 99/64625 12/1999

OTHER PUBLICATIONS

Axelrod et al, AIDS Research and Human Retroviruses 15(8), 759 (1999).*
Poeschla et al., "Development of HIV vectors for anti-HIV gene therapy," Proc. Natl. Acad. Sci., p. 11395-1139, (Oct. 1996).
Harrison et al., "Activation of a Diphtheria Toxin A Gene by Expression of Human Immunodeficiency Virus-1 Tat and Rev Proteins in Transfected Cells," Human Gene Therapy, Mary Ann Liebert, Inc. (USA), p. 53-60, (1991).
Schneider et al., "Inactivation of the Human Immunodeficiency Virus Type 1 Inhibitory Elements Allows Rev-Independent Expression of Gag and Gag/Protease and Particle Formation," Journal of Virology, American Society for Microbiology (USA), p. 4892-4903, (Jul. 1997).
Dorsky et al., "Detection of HIV-1 Infection with a Green Fluorescent Protein Reporter System," Journal of Acquired Immune Deficiency Syndromes and Human Retrovirology, Lippiocott-Raven Publishers (USA), vol. 13 (No. 4), p. 13308-1331, (1996). 13:308-313.
Gervaix et al., "A new reporter cell line to monitor HIV infection and drug susceptibility in vitro," Proc. Natl. Acad, Sci., p. 4653-4658, ( Apr. 1997).

* cited by examiner

*Primary Examiner*—James Martinell
(74) *Attorney, Agent, or Firm*—Jenkins, Wilson, Taylor & Hunt, P.A.

(57) ABSTRACT

The present invention relates to a reporter gene construct for the detection of the HIV Rev and HIV Tat proteins. Furthermore, the invention relates to a functionality test method for Rev and Rev fusion proteins prepared in a recombinant manner, a method of screening for sequences of different origin for their activity as an instability element, a method of screening for sequences which cause the transport out of the nucleus into the cytoplasm by binding to cellular or other viral shuttle proteins, as well as to a method for the detection of HIV-infected cells. The reporter gene construct according to the present invention, after it has been introduced into cells, in the presence of HIV Rev and HIV Tat proteins results in the formation of reporter proteins which may be used for quantitative/qualitative detection of the HIV Rev and HIV Tat proteins.

20 Claims, 4 Drawing Sheets

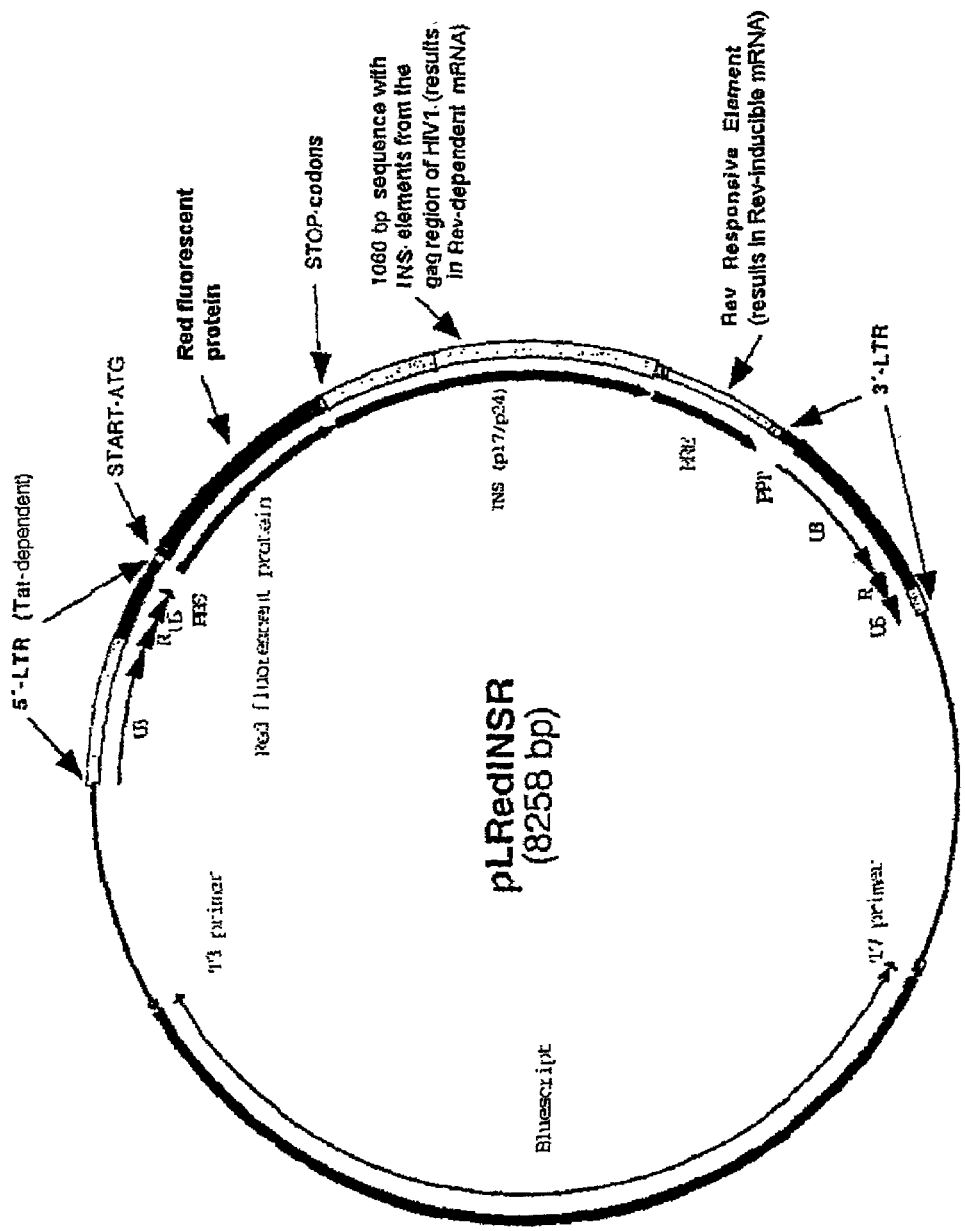
Figure 1: Reporter Construct

Figure 2: Fluorimetric detection of the expression of the early HIV proteins Rev and Tat on a single cell level
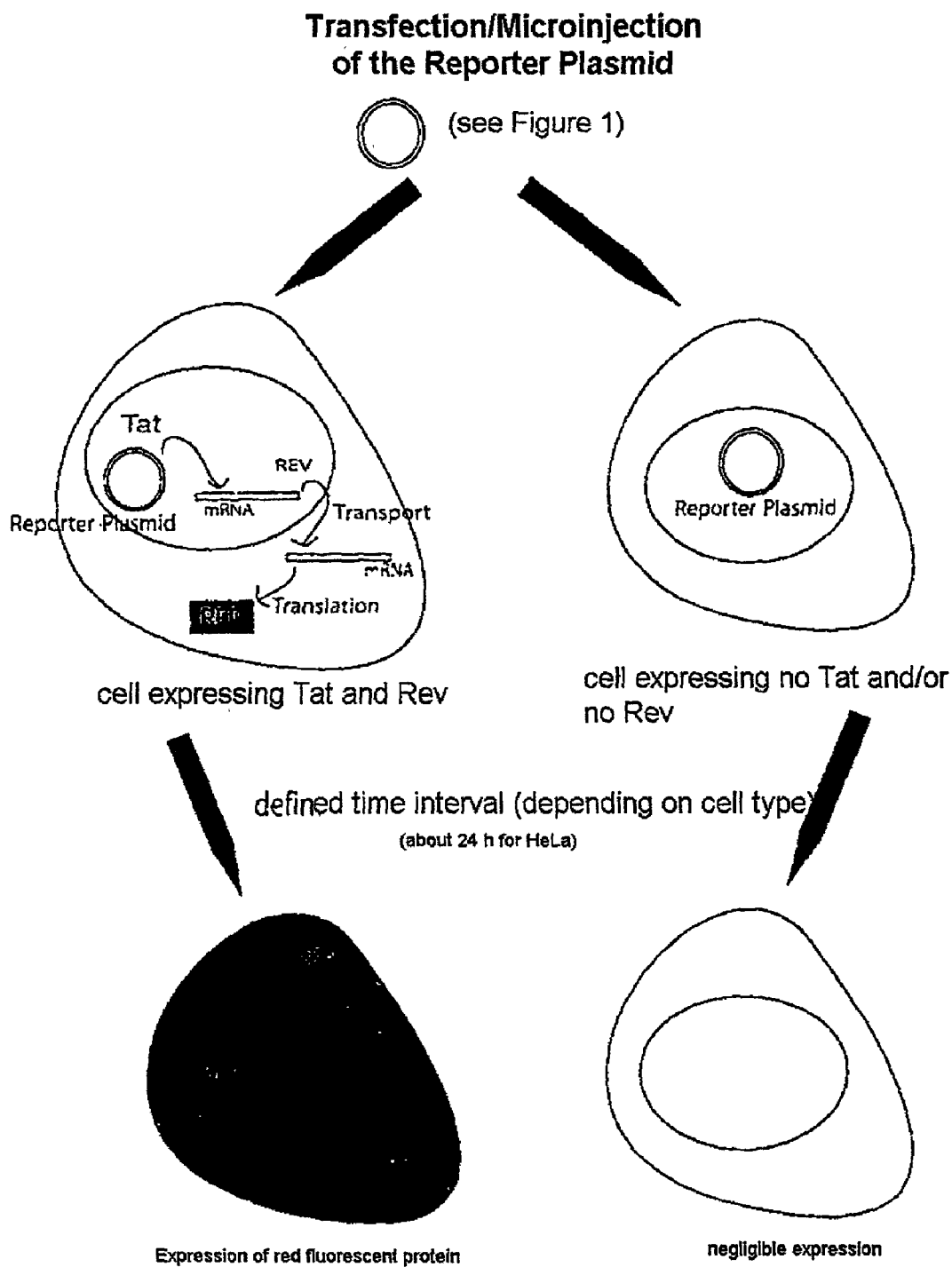

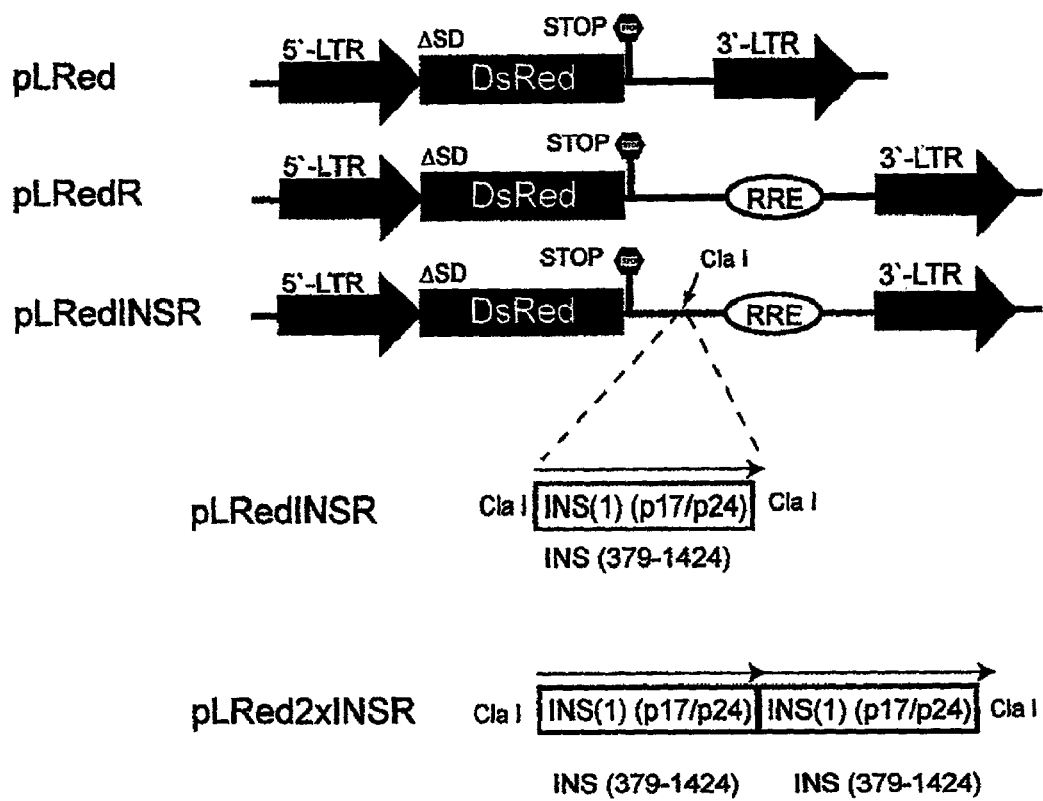
Figure 3 (plasmids)

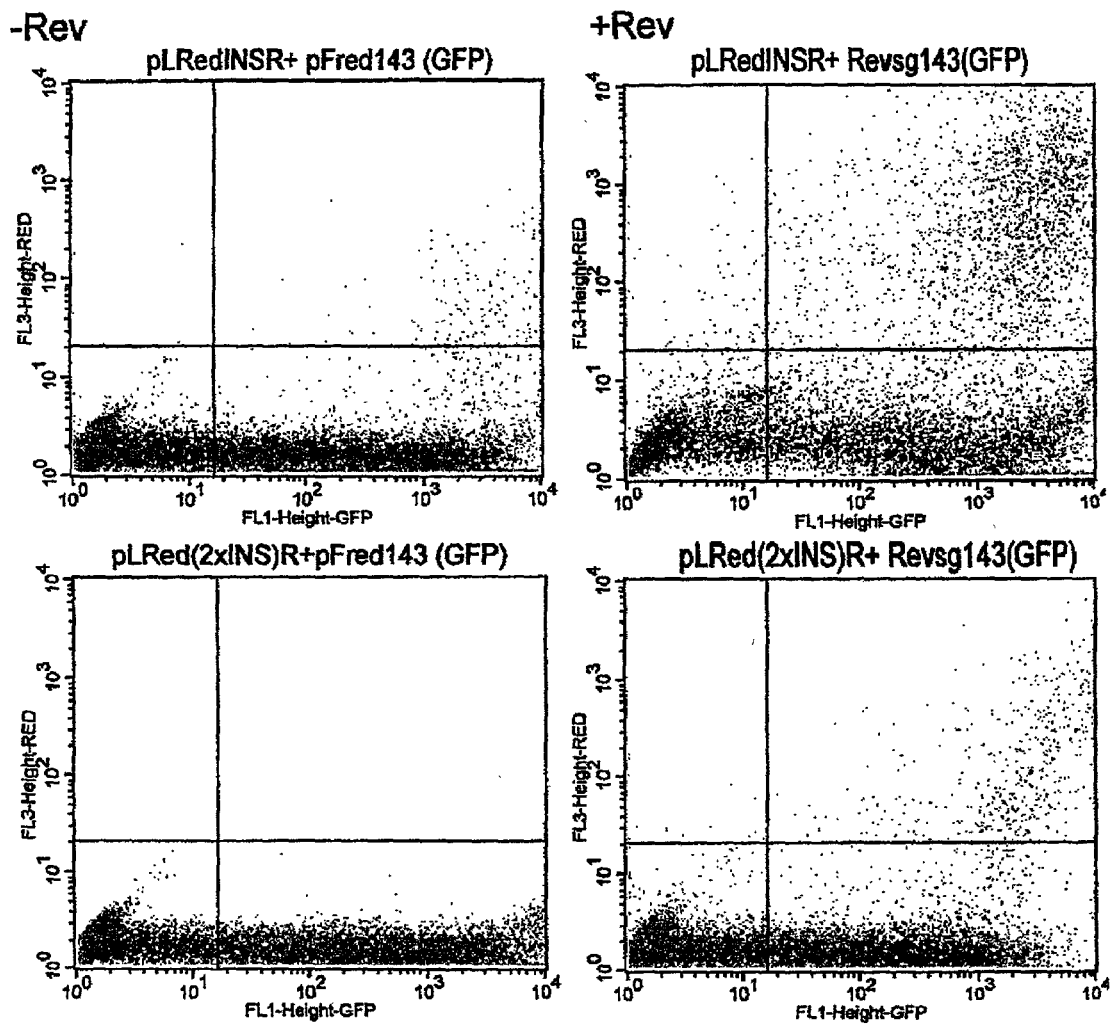
Fig. 4: the Rev-dependent expression of the reporter using pLRedINSR and pLRed2xINSR as examples.

REPORTER GENE CONSTRUCT FOR THE DETECTION OF HIV REV AND HIV TAT

TECNICAL FIELD

The present invention relates to a reporter gene construct for the detection of the HIV Rev and HIV Tat proteins. Furthermore, the invention relates to a functionality test method for Rev and Rev fusion proteins prepared by recombinant DNA technology, a method of screening for sequences of different origin for their activity as an instability element, a method of screening for those sequences causing transport out of the nucleus into the cytoplasm by binding to cellular or other viral shuttle proteins as well as to a method for the detection of HIV-infected cells.

BACKGROUND ART

Rev and Tat are regulatory factors of the human immunodeficiency virus (HIV). They are among the first proteins to be synthesized in infected cells, and both are stimulators of HIV gene expression. The biological activity of Tat and Rev is important for the amount of virus production by infected cells. For example, the low HIV production which is characteristic for human astrocytes is associated with a 10 times decreased activity of HIV Rev (Ludwig et al., 1999, J. Virol. 73:8279–8289).

This importance mentioned above of Rev and Tat for the amount of virus production renders them particularly suitable for methods for the detection of HIV infection.

At present, there are two types of REV reporter systems which use either (1) HIV Gag proteins (e.g. vector pBR37R (Ludwig et al., 1999, J. Virol. 73:8279–8289)) or (2) a heterologous protein (e.g. chloramphenicol acetyl transferase=CAT; pDM128, Hope T. J. et al., 1990) as a reporter for Rev activity. In both systems the Rev reporter protein is detected in an indirect manner, i.e. either by means of antibody-ELISA (Gag, CAT) or, in the case of pDM128, by a functional CAT test. Both reporter proteins are detected in lysates of transfected cells for which several thousands of transfected cells must be employed.

The main disadvantages of the "gag-ELISA" are the relatively high efforts with respect to time and materials, the requirement of cell lysis (no further use of the cell population is possible), and the high costs (the techniques used so far are based on detecting Rev activity by the so-called "batch" method (antigen detection in the extract of lysed cells)).

So far, there have also been approaches which only detect the above-mentioned HIV Tat protein. Reporter gene constructs have been employed for this detection which for example express green fluorescent protein under the control of HIV LTR and thus in a Tat-dependent (but Rev-independent) manner (see Dorsky et al., J Acquir Immune Defic Syndr Hum Retrovirol, 1996 Dec. 1; 13(4):308–313 *Detection of HIV-I infection with a green fluorescent protein reporter system*).

Therefore, with regard to the disadvantages cited above the object of the present invention is to provide a highly specific reporter gene construct which may be used to perform HIV Rev-and Tat-specific test assays using living cells on a single cell level in a quick and cost-effective manner.

This object has been achieved by the features indicated in the independent claims. Preferred embodiments of the invention are set forth in the dependent claims.

SUMMARY OF THE INVENTION

The invention enables the detection and quantification of the function of HIV Rev and Tat proteins in living cells on a single cell level. The test is based on a qualitative and quantitative evaluation, and possibly selection and further cultivation of Rev-containing cells by means of the expression of a reporter gene. To achieve this Rev-dependent expression of the fluorescent protein, a reporter plasmid is used which is introduced into the cells to be tested.

This reporter plasmid has the following elements in functional association:

a) a promoter;
b) a TAR (Tat activation response) element;
c) a reporter gene;
d) a HIV Rev responsive element (RRE);
e) a transcription termination signal and a polyadenylation signal.

The reporter construct according to the invention can be transferred into cells (for example by transfection, microinjection etc.), and the recipient cells are analyzed after a defined time period. This time period depends on the amount of vector, e.g. plasmid transferred, the cell type, and the amount of Tat and Rev proteins produced in the cells to be examined.

Since the presence of Tat in the cell is required to enable an efficient elongation of transcription, reasonable amounts of the reporter mRNA will only be produced in those cells which contain functional Tat. In the further course, functionally active Rev is required for the transport of the reporter mRNA into the cytoplasm which would otherwise be retained in the nucleus and would be degraded. Rev-dependence is enhanced if the reporter gene construct of the invention contains an instability element (INS) in the reporter mRNA. Only in the case of an efficient transport of the mRNA into the cytoplasm translation of the reporter gene will be apparent.

Not before both proteins Rev and Tat are present inside the cell in a functional form (as in the case of e.g. transfection of the respective expression plasmids, microinjection or transfection of the functional proteins) a strong expression of the reporter protein will be achieved. This may be documented and observed quickly and easily on single cell level and in cell populations using known procedures like fluorescence or laser scanning microscopy or flow cytometry.

An advantage of the newly developed reporter construct is its uncomplicated and cost-effective use (only one plasmid is necessary) by which almost any large number of cells may be subjected to screening. Another advantage is the fact that single cell analyses may be performed. This is of particular importance for diagnostic detection of low amounts of infected cells in patients suffering from a HIV infection. For this purpose, the method of choice is fluorescence flow cytometry which also enables the selection and further cultivation of the selected cells.

By means of the invention it is possible for the first time to measure the activity of Rev in living cells on a single cell level in a quick and cost effective manner.

The present receptor construct contains all HIV elements causing expression dependence of Tat and Rev in association with a heterologous reporter. This serves to achieve a very high specificity for the activity of these HIV factors. In contrast to present Rev reporter systems (see above) a reporter protein (encoded by a reporter gene) is used which can either be detected itself or by the formation of respective non-toxic products in living cells and therefore enables directly the detection of the reporter. These reporter proteins include for example fluorescent proteins (e.g. with red, yellow, or blue fluorescence), or enzymes metabolizing a cellular dye, or briefly all proteins which may be detected without cell fixation on a single cell level via non-toxic products. As an example for enzymes metabolizing a cellular (or cell penetrating) dye, the enzymes beta-galactosidase, beta-glucuronidase and luciferase can be used. The use of such reporter proteins also contributes to an increase in specificity and enables a quicker and more cost-effective test procedure.

The term "promoter" as used in the claims and the specification is meant to include any transcriptional control unit capable of intitiating transcription and includes regulatory elements such as enhancers and other regions binding transcriptional control factors.

The reporter gene construct according to the present invention preferably contains instability elements (INSs). These instability elements, preferably derived from HIV RNA, inhibit expression in the absence of Rev. By incorporation of these INSs into the construct downstream of the reporter, maximal inhibition of reporter expression is achieved in the absence of Rev without effecting the translation of the reporter in the presence of Rev. Thus, due to the presence of INSs, the reporter systems shown an extremely low "background" without Rev. A detailed description of the INSs may be found in the publication by Schneider R. et al., Journal of Virology, July 1997, pages 4892–4903 which is incorporated hereby by reference in its entirety.

The INS is incorporated into the reporter construct downstream of the reporter gene sequence. If a termination sequence for protein synthesis (see below) is included in the construct directly following the reporter gene sequence, the INS will be incorporated between this termination sequence and the HIV Rev responsive element (RRE) (see also FIG. 3). According to the invention, one or more INSs may be included in the construct. By repetitive inclusion of INS sequences the "background" described above may be further minimized (in this respect, see also FIG. 3).

Furthermore, the reporter gene construct preferably also contains a termination signal for protein synthesis downstream of the reporter gene sequence.

According to a preferred embodiment, the instability element is derived from the genome of HIV, e.g. from the INS portions of the gag region of HIV, and may for example consist of bases No. 379-1424 of the HIV HXB2R genome as presented in SEQ ID NO: 1 (see also Schneider et al., supra).

The reporter construct according to the invention finds use in a method for in vitro detection of HIV infected eukaryotic cells. In this method, the reporter gene construct according to the present invention is introduced into cells, the cells are harvested after a defined period of time, and eventually a determination of the presence/amount of the reporter protein will be carried out. As a defined period of time, a time interval of about 24 h has proven to be particularly advantageous. The cells, in which the inventive reporter gene construct is introduced in this case, are preferably living human cells, in which Rev and Tat are potentially expressed.

The reporter gene construct preferably encodes a fluorescent protein wherein the determination of the protein is carried out by means of fluorescence microscopy or FACS. Preferred proteins are well known fluorescent proteins like green fluorescent protein (for example, from *Aequoria victoria*) or red fluorescent protein from coral; or DsRed obtained from Clontech. Any other variation of a fluorescent protein may be considered.

Moreover, the present invention provides a method of screening for gene sequences for their activity as an instability element or as Rev responsive element (RRE). In this method, a test sequence is substituted for the instability element or the Rev responsive element (RRE) of the inventive reporter gene construct, cells are transfected with this test reporter gene construct, and eventually the expression of the reporter gene is compared to the expression of the original reporter gene construct in the presence of Tat and Rev. The term test sequence, as used in the description and the claims, encompasses all gene sequences, which theoretically could positively influence the expression and/or synthesis of the reporter gene construct of the present invention. Those test sequences might be derived, for example, from the human genome or from viral genomes.

In practice, such a screening method might be performed by providing to sets of cells, wherein one set is transfected with the inventive (original) reporter gene construct, and the other is transfected with the test reporter gene construct. Afterwards, expression of the reporter gene is compared in both sets of cells. A comparable or even higher expression of the reporter gene in the cells transfected with the test reporter gene construct indicates that the test sequence, which has been substituted for the original Rev-responsive sequences (RRE) and/or INS might have a similar function.

On the other hand, a reporter construct lacking the RRE can be used to detect novel INS elements, by assaying for diminished production of the reporter protein when comparing with a similar construct lacking the INS or containing the INS in antisense orientation.

The reporter construct can also be used for functional screening of Rev or Tat mutants or identification of other proteins of cellular or viral origins with similar functions as Tat or Rev. Furthermore, it can be used to identify Tat-responsive promoters of cellular or viral orgin Furthermore, the present invention provides a method of screening for gene sequences which cause the transport out of the nucleus by binding to cellular or other viral shuttle proteins wherein the Rev responsive element of the reporter gene construct according to the invention is replaced by a test sequence and afterwards cells are transfected with this reporter gene construct, and the expression of this test reporter gene is compared to the expression of the original reporter gene construct in the presence of Tat and Rev.

If test sequences have been tested positive in the above described methods, this information is of importance for the understanding of regulatory and cell biological processes, the modulation of expression levels of transgenes for stable expression. A transgene in this context is defined as a gene (in form of a suitable gene construct), which has been transferred from one species to another.

Further, there is provided an expression vector containing a reporter gene construct according to the present invention, an eukaryotic or prokaryotic cell transformed by this expression vector as well as RNA produced by the transcription of one of the expression vectors according to the invention.

Representative examples of appropriate cells, in which the reporter gene construct is introduced in the above described methods (not including the method for HIV detection, which utilizes human cells) are including bacterial cells, such as *Streptococci, Staphylococci, E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used, which incorporate the reporter gene construct, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL, 2nd Ed., Cold Spring Harbor Laboratory Press, Cold Spring Harbor, N.Y. (1989).

Generally, introduction of the reporter gene construct into the above described cells can be effected by methods described in many standard laboratory manuals, such as Davis et al., Basic Methods in Molecular Biology (1986) and Sambrook et al., Molecular Cloning: A Laboratory Manual, (supra). Preferred such methods include, for instance, calcium phosphate transfection, DEAF-dextran mediated transfection, transvection, microinjection, cationic lipid-mediated transfection, electroporation, transduction, scrape loading, ballistic introduction or infection.

Finally, the present invention comprises a functionality test for Rev and Rev fusion proteins prepared in a recombinant manner wherein cells are transfected with a reporter gene construct according to the invention and wherein the cells are co-transfected with an expression plasmid, or the test is carried out in a cell line expressing Tat in a stable manner.

BRIEF DESCRIPTION OF THE DRAWINGS

FIG. 1 shows a reporter gene construct according to the present invention.

FIG. 2 shows a diagram of the fluorimetric detection of the expression of the early HIV proteins Rev and Tat on a single cell level.

FIG. 3 shows a comparison of the plasmids pLRed, pLRedR, pLRedINSR, and pLRed2xINSR.

FIG. 4 shows the Rev-dependent expression of the reporter using pLRedINSR and pLRed2xINSR as examples.

DETAILED DESCRIPTION OF THE INVENTION

Referring to an embodiment of the invention, FIG. 1 shows a reporter construct according to the invention which contains, together with the reporter gene, the RNA binding element for Rev (called RRE=Rev responsive element), and HIV RNA elements (so-called instability elements=INSs) inhibiting the expression in the absence of Rev. By incorporating these INSs into the system according to the invention downstream of the termination signal for the reporter, maximal inhibition of reporter expression in the absence of Rev is achieved without affecting reporter translation in the presence of Rev.

Into the present embodiment, a portion of the HIV gag gene has been introduced in which several INSs have been identified so far (Schneider et al., 1997). In the reporter construct according to the present invention the INSs are localized outside of the regions encoding the reporter and therefore do not affect the synthesis of the reporter on a translational level.

The reporter construct depicted in FIG. 1 consists of the following elements:

5'-LTR: contains the transcriptional regulatory unit (promoter/enhancer) and, 3' of the mRNA start site, the TAR (Tat activation response element) to which the Tat HIV protein binds. Tat is required for efficient elongation of the mRNA transcripts Red: Red fluorescent protein (in this case: DsRed obtained form Clontech; any other variation of a fluorescent protein may be considered; however certain variations (green, red) are preferable for subsequent FACS analyses). Downstream of the gene sequence encoding the red fluorescent protein there are STOP codons (termination signals) so that the translation will always end at this point and DsRed will be the only protein expressed observed in the assays (S1). The gene has been amplified from vector pDSRed1-N1 commercially available from CLONTECH.

P17/24: 1060 bp region derived form the gag portion of HIV (bases No. 379–1424 of the genome of HXB2R). The so-called INS regions contained therein render the mRNA unstable in the absence of Rev, i.e. inhibit the efficient transport of the mRNA into the cytoplasm by the machinery of the cell.

RRE: Rev responsive element; contains the binding site for the viral shuttle protein Rev thereby enabling it to transport the mRNA into the cytoplasm and prevent its degradation in the nucleus.

3'-LTR: End of transcription and mRNA polyadenylation signal

As depicted in FIG. 2, cells are transfected, microinjected etc. by means of the reporter construct according to the invention, and these cells are harvested and analyzed after a defined time point. This time point depends on the amount of plasmid transfected, the cell type, and the amount of Tat and Rev proteins in the cells to be examined. For typical cell culture experiments, a time interval of 24 h will be optimal.

Since the presence of Tat in the cell is required to enable an efficient elongation of transcription reasonable amounts of the reporter mRNA will only be produced in those cells which contain functional Tat.

In the further course, functionally active Rev is required for the transport of the reporter mRNA into the cytoplasm which would otherwise by retained in the nucleus due to the instability elements contained on the mRNA and be degraded. Only in the case of an efficient transport of the mRNA into the cytoplasm translation of the red fluorescent protein will be initiated.

Not before both proteins Rev and Tat are present inside the cell in a functional form (as in the case of e.g. transfection of the respective expression plasmids, microinjection or transfection of the functional proteins) a strong expression of the fluorescent protein will be achieved. This fluorescence may be documented and observed quickly and easily on a single cell level using a fluorescence microscope or a FACS.

FIG. 4 shows a schematic representation of the Rev-dependence of two reporter constructs by means of FACS analysis. HeLa Tat cells were transfected with a reporter construct (upper FACS plots: pLRedINSR; lower FACS plots: pLRed(2xINS)R) and each with a green fluorescent transfection control (left plots) and a green fluorescent Rev fusion protein (right plots). Cells which are strongly positive for expression of the red fluorescent reporter are localized high up in the right upper quadrant. Transfected cells which are positive only for the constitutively expressed transfection control are localized in the lower right quadrant. Untransfected cells are in the lower left quadrant. It is clearly seen that in the presence of Rev far more reporter protein is expressed and that the two constructs differ in their Rev-dependence (the construct of the lower plots is much more dependent on Rev).

EXAMPLE

In an experiment, HeLa cells were transfected with different combinations of the plasmids described and analyzed for the expression of fluorescent proteins.

HeLa cells were transfected with the constructs described and analyzed by means of FACS analysis:

FACS Analysis:

For the analysis of the Tat- and Rev-dependent expression of the fluorescent reporters, HeLa and HeLaTat cells were used.

Cells were seeded into 60 mm culture dishes and transfected after 24 h with the reporter constructs and a transfection control (GFP), and with the reporter constructs together with an expression construct for a Rev-GFP fusion protein, respectively, using different methods. The method used was calcium phosphate co-precipitation (Cell Phect, Amersham Pharmacia) and FuGene (Roche). The results obtained were independent of the method used.

24 hours following transfection the cells were harvested, resuspended in PBS and then subjected to FACS analysis (FACS plots: see FIGS. F1 and F2). The analyses were carried out using a Calibur FACS device and CellQuest software of Becton Dickinson company.

For the evaluation, between 20,000 and 100,000 cells of a healthy homogenous cell population were examined for their fluorescence. For this purpose, the green fluorescence of the transfection control and the Rev-GFP fusion protein, respectively, were plotted against the red fluorescence of the reporter protein in a 2D plot. For the evaluation, the number of green fluorescent cells showing a strong red fluorescence was determined. Repeated experiments showed that the expression of the reporter depends strongly (pLREdINSR) and extremely strongly (pLRed(2xINS)R), respectively, on the presence of Rev. In the case of the reporter pLRed (2xINS)R no unspecific background could be observed in the experiments performed.

As has also been demonstrated, the presence of Tat is a prerequisite for these experiments

What is claimed is:

1. A reporter gene construct containing the following elements in 5' to 3' order:
    (a) a promoter;
    (b) a TAR (Tat activation response) element;
    (c) a reporter gene;
    (d) the Rev responsive element (RRE) of HIV;
    (e) a transcription termination signal and a polyadenylation signal.

2. The reporter gene construct of claim 1, further comprising a protein synthesis termination signal downstream of the reporter gene sequence.

3. The reporter gene construct of claim 1, further comprising one or more instability elements (INSs) downstream of the reporter gene.

4. The reporter gene construct of claim 1, wherein the reporter gene encodes a fluorescent protein.

5. The reporter gene construct of claim 4, wherein the reporter gene encodes a red fluorescent protein.

6. The reporter gene construct of claim 3, wherein the instability element is derived from a HIV genome.

7. The reporter gene construct of claim 6, wherein the instability element comprises at least one INS sequence of a gag region of an HIV genome as set forth in SEQ ID NO: 1.

8. The reporter gene construct of claim 7, wherein the instability element consists of bases No. 379-1424 of the genome of HIV HXB2R as presented in SEQ ID NO: 1.

9. A method for the in vitro detection of HIV-infected eukaryotic cells wherein
    a) a reporter gene construct according to claim 1 is introduced into the cells;
    b) the cells are harvested after a defined time period; and c) a determination of the presence/quantity of the reporter protein is carried out.

10. The method of claim 9, wherein the reporter gene construct encodes a fluorescent protein, and wherein the determining is by fluorescence microscopy or FACS.

11. The method of claim 9, wherein the defined time period is about 24 hours.

12. A method of screening a gene sequence for activity as an instability element, the method comprising:
   (a) replacing one or more of the instability elements of the reporter gene construct of claim 3 with a test sequence, thereby forming a test reporter gene construct;
   (b) introducing the test reporter gene construct into a cell; and
   (c) comparing expression of the reporter gene of the test reporter gene construct of step (a) to expression of the reporter gene construct according to claim 3 in the presence of Tat and Rev.

13. A method of screening for gene sequences which cause transport out of the nucleus of a reporter gene mRNA by binding to cellular or other viral shuffle proteins, the method comprising:
   (a) replacing the Rev responsive element of the reporter gene construct of claim 1 with a test sequence to produce a test reporter gene construct;
   (b) introducing the test reporter gene construct into a cell;
   (c) comparing expression of the reporter gene of the test reporter gene construct to expression of the reporter gene construct of claim 1 in the presence of Tat and Rev.

14. An expression vector comprising a reporter gene construct of claim 1.

15. A eukaryotic or prokaryotic cell transformed by an expression vector of claim 14.

16. A method for functionality testing of Rev and recombinant Rev fusion proteins, the method comprising:
   (a) introducing a reporter gene construct of claim 1 into a cell comprising a Tat protein; and afterwards
   (b) harvesting the cell after a defined time period; and
   (c) determining the presence or quantity of reporter protein encoded by the reporter gene construct in the cell.

17. A method of screening for Rev or Tat mutants or for identifying other proteins of cellular or viral origin with similar functions as Tat or Rev, the method comprising:
   (a) introducing a reporter gene construct of claim 1 into a cell; and
   (b) comparing expression of the reporter gene of the reporter gene construct in said cell in the presence of Tat and Rev to that of the reporter gene construct in the presence of Rev or Tat mutants or said other proteins of cellular or viral origins with similar functions as Tat or Rev, wherein Tat enables elongation of transcription of the reporter gene mRNA and Rev causes transport of the reporter gene mRNA out of the cell's nucleus and into the cell's cytoplasm.

18. The method of claim 16, wherein the cell stably expresses a Tat protein.

19. The method of claim 16, wherein the Tat protein is encoded by a Tat expression plasmid and the Tat expression plasmid is co-transfected into the cell with a reporter gene construct comprising the following elements in 5' to 3 order:
   (a) a promoter;
   (b) a TAR (Tat activation response) element;
   (c) a reporter gene;
   (d) the Rev responsive element (RRE) of HIV;
   (e) a transcription termination signal and a polyadenylation signal.

20. The method of claim 16, wherein the cell comprises a recombinant Tat protein.

* * * * *

SEQUENCE LISTING

```
<160> NUMBER OF SEQ ID NOS: 1

<210> SEQ ID NO 1
<211> LENGTH: 9719
<212> TYPE: DNA
<213> ORGANISM: Human immunodeficiency virus
<300> PUBLICATION INFORMATION:
<308> DATABASE ACCESSION NUMBER: Genbank/K03455
<309> DATABASE ENTRY DATE: 1997-03-25
<313> RELEVANT RESIDUES: (379)..(1424)

<400> SEQUENCE: 1
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta gaagaagcca     180
acaaaggaga gaacaccagc ttgttacacc ctgtgagcct gcatggaatg gatgacccgg     240
agagagaagt gttagagtgg aggtttgaca gccgcctagc atttcatcac atggcccgag     300
agctgcatcc ggagtacttc aagaactgct gacatcgagc ttgctacaag ggactttccg     360
ctggggactt tccaggagg cgtggcctgg gcgggactgg ggagtggcga gccctcagat     420
cctgcatata agcagctgct ttttgcctgt actgggtctc tctggttaga ccagatctga     480
gcctgggagc tctctggcta actagggaac ccactgctta agcctcaata aagcttgcct     540
tgagtgcttc aagtagtgtg tgcccgtctg ttgtgtgact ctggtaacta gagatccctc     600 agacccttt agtcagtgtg gaaaatctct agcagtggcg cccgaacagg gacctgaaag     660 cgaaaggaa accagaggag ctctctcgac gcaggactcg gcttgctgaa gcgcgcacgg     720
caagaggcga ggggcggcga ctggtgagta cgccaaaaat tttgactagc ggaggctaga     780
aggagagaga tgggtgcgag agcgtcagta ttaagcgggg gagaattaga tcgatgggaa     840
aaaattcggt taaggccagg gggaaagaaa aaatataaat taaaacatat agtatgggca     900
agcagggagc tagaacgatt cgcagttaat cctggcctgt tagaaacatc agaaggctgt     960
```

-continued

```
agacaaatac tgggacagct acaaccatcc cttcagacag gatcagaaga acttagatca    1020
ttatataata cagtagcaac cctctattgt gtgcatcaaa ggatagagat aaaagacacc    1080
aaggaagctt tagacaagat agaggaagag caaaacaaaa gtaagaaaaa agcacagcaa    1140
gcagcagctg acacaggaca cagcaatcag gtcagccaaa attaccctat agtgcagaac    1200
atccaggggc aaatggtaca tcaggccata tcacctagaa cttttaaatgc atgggtaaaa    1260 gtagtagaag agaaggcttt cagcccagaa gtgatacccca tgttttcagc attatcagaa    1320
ggagccaccc cacaagattt aaacaccatg ctaaacacag tggggggaca tcaagcagcc    1380
atgcaaatgt taaaagagac catcaatgag gaagctgcag aatgggatag agtgcatcca    1440
gtgcatgcag ggcctattgc accaggccag atgagagaac caaggggaag tgacatagca    1500
ggaactacta gtacccttca ggaacaaata ggatggatga caaataatcc acctatccca    1560
gtaggagaaa tttataaaag atggataatc ctgggattaa ataaaatagt aagaatgtat    1620
agccctacca gcattctgga cataagacaa ggaccaaagg aacccttag agactatgta    1680 gaccggttct ataaaactct aagagccgag caagcttcac aggaggtaaa aaattggatg    1740
acagaaacct tgttggtcca aaatgcgaac ccagattgta agactatttt aaaagcattg    1800
ggaccagcgg ctacactaga agaaatgatg acagcatgtc agggagtagg aggacccggc    1860
cataaggcaa gagttttggc tgaagcaatg agccaagtaa caaattcagc taccataatg    1920
atgcagagag gcaattttag gaaccaaaga aagattgtta agtgtttcaa ttgtggcaaa    1980
gaagggcaca cagccagaaa ttgcagggcc cctaggaaaa agggctgttg gaaatgtgga    2040
aaggaaggac accaaatgaa agattgtact gagagacagg ctaatttttt agggaagatc    2100
tggccttcct acaagggaag gccagggaat tttcttcaga gcagaccaga gccaacagcc    2160
ccaccagaag agagcttcag gtctggggta gagacaacaa ctcccccctca gaagcaggag    2220 ccgatagaca aggaactgta tcctttaact tccctcaggt cactctttgg caacgacccc    2280
tcgtcacaat aaagataggg gggcaactaa aggaagctct attagataca ggagcagatg    2340
atacagtatt agaagaaatg agtttgccag gaagatggaa accaaaaatg ataggggaa    2400 ttggaggttt tatcaaagta agacagtatg atcagatact catagaaatc tgtggacata    2460
aagctatagg tacagtatta gtaggaccta cacctgtcaa cataattgga agaaatctgt    2520
tgactcagat tggttgcact ttaaattttc ccattagccc tattgagact gtaccagtaa    2580
aattaaagcc aggaatggat ggcccaaaag ttaaacaatg gccattgaca gaagaaaaaa    2640
taaaagcatt agtagaaatt tgtacagaga tggaaaagga agggaaaatt tcaaaaattg    2700
ggcctgaaaa tccatacaat actccagtat ttgccataaa gaaaaaagac agtactaaat    2760
ggagaaaatt agtagatttc agagaactta ataagagaac tcaagacttc tgggaagttc    2820
aattaggaat accacatccc gcagggttaa aaaagaaaaa atcagtaaca gtactggatg    2880
tgggtgatgc atatttttca gttcccttag atgaagactt caggaagtat actgcattta    2940
ccatacctag tataaacaat gagacaccag ggattagata tcagtacaat gtgcttccac    3000
agggatggaa aggatcacca gcaatattcc aaagtagcat gacaaaaatc ttagagcctt    3060
ttagaaaaca aaatccagac atagttatct atcaatacat ggatgatttg tatgtaggat    3120
ctgacttaga aatagggcag catagaacaa aaatagagga gctgagacaa catctgttga    3180
ggtggggact taccacacca gacaaaaaac atcagaaaga acctccattc ctttggatgg    3240
gttatgaact ccatcctgat aaatggacag tacagcctat agtgctgcca gaaaaagaca    3300
```

```
gctggactgt caatgacata cagaagttag tggggaaatt gaattgggca agtcagattt     3360
acccagggat taaagtaagg caattatgta aactccttag aggaaccaaa gcactaacag     3420
aagtaatacc actaacagaa gaagcagagc tagaactggc agaaaacaga gagattctaa     3480
aagaaccagt acatggagtg tattatgacc catcaaaaga cttaatagca gaaatacaga     3540
agcaggggca aggccaatgg acatatcaaa tttatcaaga gccatttaaa aatctgaaaa     3600
caggaaaata tgcaagaatg aggggtgccc acactaatga tgtaaaacaa ttaacagagg     3660
cagtgcaaaa aataaccaca gaaagcatag taatatgggg aaagactcct aaatttaaac     3720
tgcccataca aaaggaaaca tgggaaacat ggtggacaga gtattggcaa gccacctgga     3780
ttcctgagtg ggagtttgtt aatacccctc ccttagtgaa attatggtac cagttagaga     3840
aagaacccat agtaggagca gaaaccttct atgtagatgg ggcagctaac agggagacta     3900
aattaggaaa agcaggatat gttactaata gaggaagaca aaaagttgtc accctaactg     3960
acacaacaaa tcagaagact gagttacaag caatttatct agctttgcag gattcgggat     4020
tagaagtaaa catagtaaca gactcacaat atgcattagg aatcattcaa gcacaaccag     4080
atcaaagtga atcagagtta gtcaatcaaa taatagagca gttaataaaa aaggaaaagg     4140
tctatctggc atgggtacca gcacacaaag gaattggagg aaatgaacaa gtagataaat     4200
tagtcagtgc tggaatcagg aaagtactat ttttagatgg aatagataag gcccaagatg     4260
aacatgagaa atatcacagt aattggagag caatggctag tgattttaac ctgccacctg     4320
tagtagcaaa agaaatagta gccagctgtg ataaatgtca gctaaaagga gaagccatgc     4380
atggacaagt agactgtagt ccaggaatat ggcaactaga ttgtacacat ttagaaggaa     4440
aagttatcct ggtagcagtt catgtagcca gtggatatat agaagcagaa gttattccag     4500
cagaaacagg gcaggaaaca gcatattttc ttttaaaatt agcaggaaga tggccagtaa     4560
aaacaataca tactgacaat ggcagcaatt tcaccggtgc tacggttagg gccgcctgtt     4620
ggtgggcggg aatcaagcag gaatttggaa ttccctacaa tccccaaagt caaggagtag     4680
tagaatctat gaataaagaa ttaaagaaaa ttataggaca ggtaagagat caggctgaac     4740
atcttaagac agcagtacaa atggcagtat tcatccacaa ttttaaaaga aaggggggga     4800
ttggggggta cagtgcaggg gaaagaatag tagacataat agcaacagac atacaaacta     4860
aagaattaca aaaacaaatt acaaaaattc aaaattttcg ggtttattac agggacagca     4920
gaaatccact ttggaaagga ccagcaaagc tcctctggaa aggtgaaggg gcagtagtaa     4980
tacaagataa tagtgacata aaagtagtgc caagaagaaa agcaaagatc attagggatt     5040
atggaaaaca gatggcaggt gatgattgtg tggcaagtag acaggatgag gattagaaca     5100
tggaaaagtt tagtaaaaca ccatatgtat gtttcaggga aagctagggg atggttttat     5160
agacatcact atgaaagccc tcatccaaga ataagttcag aagtacacat cccactaggg     5220
gatgctagat tggtaataac aacatattgg ggtctgcata caggagaaag agactggcat     5280
ttgggtcagg gagtctccat agaatggagg aaaagagat atagcacaca agtagaccct     5340
gaactagcag accaactaat tcatctgtat tactttgact gtttttcaga ctctgctata     5400
agaaaggcct tattaggaca catagttagc cctaggtgtg aatatcaagc aggacataac     5460
aaggtaggat ctctacaata cttggcacta gcagcattaa taacaccaaa aaagataaag     5520
ccacctttgc ctagtgttac gaaactgaca gaggatagat ggaacaagcc ccagaagacc     5580
aagggccaca gagggagcca cacaatgaat ggacactaga gcttttagag gagcttaaga     5640
atgaagctgt tagacatttt cctaggattt ggctccatgg cttagggcaa catatctatg     5700
```

-continued

```
aaacttatgg ggatacttgg gcaggagtgg aagccataat aagaattctg caacaactgc   5760
tgtttatcca ttttcagaat tgggtgtcga catagcagaa taggcgttac tcgacagagg   5820
agagcaagaa atggagccag tagatcctag actagagccc tggaagcatc caggaagtca   5880
gcctaaaact gcttgtacca attgctattg taaaaagtgt tgctttcatt gccaagtttg   5940
tttcataaca aaagccttag gcatctccta tggcaggaag aagcggagac agcgacgaag   6000
agctcatcag aacagtcaga ctcatcaagc ttctctatca aagcagtaag tagtacatgt   6060
aacgcaacct ataccaatag tagcaatagt agcattagta gtagcaataa taatagcaat   6120
agttgtgtgg tccatagtaa tcatagaata taggaaaata ttaagacaaa gaaaatagac   6180
caggttaatt gatagactaa tagaaagagc agaagacagt ggcaatgaga gtgaaggaga   6240
aatatcagca cttgtggaga tggggtggga gatggggcac catgctcctt gggatgttga   6300
tgatctgtag tgctacagaa aaattgtggg tcacagtcta ttatgggtac ctgtgtgga   6360
aggaagcaac caccactcta ttttgtgcat cagatgctaa agcatatgat acagaggtac   6420
ataatgtttg ggccacacat gcctgtgtac ccacagaccc caacccacaa gaagtagtat   6480
tggtaaatgt gacagaaaat tttaacatgt ggaaaaatga catggtagaa cagatgcatg   6540
aggatataat cagtttatgg gatcaaagcc taaagccatg tgtaaaatta accccactct   6600
gtgttagttt aaagtgcact gatttgaaga atgatactaa taccaatagt agtagcggga   6660
gaatgataat ggagaaagga gagataaaaa actgctcttt caatatcagc acaagcataa   6720
gaggtaaggt gcagaaagaa tatgcatttt tttataaact tgatataata ccaatagata   6780
atgatactac cagctataag ttgacaagtt gtaacacctc agtcattaca caggcctgtc   6840
caaaggtatc ctttgagcca attcccatac attattgtgc cccggctggt tttgcgattc   6900
taaaatgtaa taataagacg ttcaatggaa caggaccatg tacaaatgtc agcacagtac   6960
aatgtacaca tggaattagg ccagtagtat caactcaact gctgttaaat ggcagtctag   7020
cagaagaaga ggtagtaatt agatctgtca atttcacgga caatgctaaa accataatag   7080
tacagctgaa cacatctgta gaattaattg tacaagacc caacaacaat acaagaaaaa   7140
gaatccgtat ccagagagga ccagggagag catttgttac aataggaaaa ataggaaata   7200
tgagacaagc acattgtaac attagtagag caaaatggaa taacactttta aaacagatag   7260
ctagcaaatt aagagaacaa tttggaaata taaaacaat aatctttaag caatcctcag   7320
gaggggaccc agaaattgta acgcacagtt ttaattgtgg aggggaattt ttctactgta   7380
attcaacaca actgtttaat agtacttggt ttaatagtac ttggagtact gaagggtcaa   7440
ataacactga aggaagtgac acaatcaccc tcccatgcag aataaaacaa attataaaca   7500
tgtggcagaa agtaggaaaa gcaatgtatg cccctcccat cagtggacaa attagatgtt   7560
catcaaatat tacagggctg ctattaacaa gagatggtgg taatagcaac aatgagtccg   7620
agatcttcag acctggagga ggagatatga gggacaattg gagaagtgaa ttatataaat   7680
ataaagtagt aaaaattgaa ccattaggag tagcacccac caaggcaaag agaagagtgg   7740
tgcagagaga aaaaagagca gtgggaatag gagctttgtt ccttgggttc ttgggagcag   7800
caggaagcac tatgggcgca gcctcaatga cgctgacggt acaggccaga caattattgt   7860
ctggtatagt gcagcagcag aacaatttgc tgagggctat tgaggcgcaa cagcatctgt   7920
tgcaactcac agtctgggc atcaagcagc tccaggcaag aatcctggct gtggaaagat   7980
acctaaagga tcaacagctc ctggggattt ggggttgctc tggaaaactc atttgcacca   8040
```

```
ctgctgtgcc ttggaatgct agttggagta ataaatctct ggaacagatt tggaatcaca    8100
cgacctggat ggagtgggac agagaaatta acaattacac aagcttaata cactccttaa    8160
ttgaagaatc gcaaaaccag caagaaaaga atgaacaaga attattggaa ttagataaat    8220
gggcaagttt gtggaattgg tttaacataa caaattggct gtggtatata aaattattca    8280
taatgatagt aggaggcttg gtaggtttaa gaatagtttt tgctgtactt tctatagtga    8340
atagagttag gcagggatat tcaccattat cgtttcagac ccacctccca accccgaggg    8400
gacccgacag gcccgaagga atagaagaag aaggtggaga gagagacaga gacagatcca    8460
ttcgattagt gaacggatcc ttggcactta tctgggacga tctgcggagc ctgtgcctct    8520
tcagctacca ccgcttgaga gacttactct tgattgtaac gaggattgtg gaacttctgg    8580
gacgcagggg gtgggaagcc ctcaaatatt ggtggaatct cctacagtat tggagtcagg    8640
aactaaagaa tagtgctgtt agcttgctca atgccacagc catagcagta gctgagggga    8700
cagatagggt tatagaagta gtacaaggag cttgtagagc tattcgccac atacctagaa    8760
gaataagaca gggcttggaa aggattttgc tataagatgg gtggcaagtg gtcaaaaagt    8820
agtgtgattg gatggcctac tgtaagggaa agaatgagac gagctgagcc agcagcagat    8880
agggtgggag cagcatctcg agacctggaa aaacatggag caatcacaag tagcaataca    8940
gcagctacca atgctgcttg tgcctggcta gaagcacaag aggaggagga ggtgggtttt    9000
ccagtcacac ctcaggtacc tttaagacca atgacttaca aggcagctgt agatcttagc    9060 cacttttaa aagaaaaggg gggactggaa gggctaattc actcccaaag aagacaagat    9120
atccttgatc tgtggatcta ccacacacaa ggctacttcc ctgattagca gaactacaca    9180
ccagggccag gggtcagata tccactgacc tttggatggt gctacaagct agtaccagtt    9240
gagccagata agatagaaga ggccaataaa ggagagaaca ccagcttgtt acaccctgtg    9300
agcctgcatg ggatggatga cccggagaga gaagtgttag agtggaggtt tgacagccgc    9360
ctagcatttc atcacgtggc ccgagagctg catccggagt acttcaagaa ctgctgacat    9420
cgagcttgct acaagggact ttccgctggg gactttccag ggaggcgtgg cctgggcggg    9480
actggggagt ggcgagccct cagatcctgc atataagcag ctgctttttg cctgtactgg    9540
gtctctctgg ttagaccaga tctgagcctg ggagctctct ggctaactag ggaacccact    9600
gcttaagcct caataaagct tgccttgagt gcttcaagta gtgtgtgccc gtctgttgtg    9660
tgactctggt aactagagat ccctcagacc cttttagtca gtgtggaaaa tctctagca    9719
```